United States Patent
Behnke, II et al.

(10) Patent No.: US 9,095,359 B2
(45) Date of Patent: Aug. 4, 2015

(54) TISSUE ABLATION SYSTEM WITH ENERGY DISTRIBUTION

(75) Inventors: Robert J. Behnke, II, Erie, CO (US); Mani N. Prakash, Boulder, CO (US); Jeffrey L. Jensen, Boulder, CO (US); Francesca Rossetto, Longmont, CO (US); Joseph D. Brannan, Erie, CO (US)

(73) Assignee: Covidien LP, Mansfield, MA (US)

( * ) Notice: Subject to any disclaimer, the term of this patent is extended or adjusted under 35 U.S.C. 154(b) by 1151 days.

(21) Appl. No.: 12/562,842

(22) Filed: Sep. 18, 2009

(65) Prior Publication Data
US 2011/0071512 A1 Mar. 24, 2011

(51) Int. Cl.
*A61B 18/18* (2006.01)
*A61N 5/02* (2006.01)
*A61B 18/00* (2006.01)

(52) U.S. Cl.
CPC ............. *A61B 18/1815* (2013.01); *A61N 5/02* (2013.01); *A61B 2018/0019* (2013.01)

(58) Field of Classification Search
CPC ............. A61B 18/18; A61B 18/1815; A61B 2018/00654; A61B 2018/0075; A61B 2018/00869; A61B 2018/1869; A61B 2018/1892; A61N 5/0455
USPC .......... 606/32, 42, 33; 607/98–100, 115, 154, 607/156
See application file for complete search history.

(56) References Cited

U.S. PATENT DOCUMENTS

| 4,292,960 A * | 10/1981 | Paglione ............................ 600/2 |
| 4,448,198 A | 5/1984 | Turner |
| 4,632,128 A | 12/1986 | Paglione et al. |
| 4,672,980 A | 6/1987 | Turner |
| 4,741,348 A * | 5/1988 | Kikuchi et al. ................ 607/102 |
| 4,815,479 A * | 3/1989 | Carr ............................... 607/102 |
| 4,860,752 A | 8/1989 | Turner |
| 5,097,844 A * | 3/1992 | Turner ........................... 607/156 |
| 5,354,325 A | 10/1994 | Chive et al. |
| 6,208,903 B1 * | 3/2001 | Richards et al. ............... 607/101 |
| 6,347,251 B1 * | 2/2002 | Deng ............................. 607/101 |
| 7,128,739 B2 | 10/2006 | Prakash et al. |
| 7,197,363 B2 | 3/2007 | Prakash et al. |
| 7,294,127 B2 | 11/2007 | Leung et al. |
| 2006/0200120 A1 * | 9/2006 | DiCarlo et al. ................. 606/41 |
| 2008/0147056 A1 | 6/2008 | Van Der Weide |

(Continued)

FOREIGN PATENT DOCUMENTS

| DE | 390937 | 3/1924 |
| DE | 1099658 | 2/1961 |

(Continued)

OTHER PUBLICATIONS

International Search Report EP10009731 dated Jan. 28, 2011.

(Continued)

*Primary Examiner* — Michael Peffley
*Assistant Examiner* — Thomas Giuliani

(57) ABSTRACT

A microwave ablation system includes an energy source adapted to generate microwave energy and a power splitting device having an input adapted to connect to the energy source and a plurality of outputs. The plurality of outputs are configured to be coupled to a corresponding plurality of energy delivery devices. The power splitting device is configured to selectively divide energy provided from the energy source between the plurality of energy devices.

14 Claims, 4 Drawing Sheets

(56) References Cited

U.S. PATENT DOCUMENTS

| | | | | |
|---|---|---|---|---|
| 2009/0326620 | A1* | 12/2009 | Rossetto et al. | 607/101 |
| 2010/0030206 | A1* | 2/2010 | Brannan et al. | 606/33 |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10328514 | 3/2005 |
| DE | 102004022206 | 12/2005 |
| DE | 202005015147 | 3/2006 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 1 159 926 | 5/2001 |
| EP | 2149343 | 2/2010 |
| FR | 179 607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| JP | 5-5106 | 1/1993 |
| JP | 05-40112 | 2/1993 |
| JP | 6-503028 | 4/1994 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| SU | 166452 | 11/1964 |
| SU | 401367 | 11/1974 |
| SU | 727201 | 4/1980 |

OTHER PUBLICATIONS

U.S. Appl. No. 08/483,742, filed Jun. 7, 1995.
U.S. Appl. No. 08/136,098, filed Oct. 14, 1993.
U.S. Appl. No. 12/129,482, filed May 29, 2008.
U.S. Appl. No. 12/135,425, filed Jun. 9, 2008.
U.S. Appl. No. 12/135,690, filed Jun. 9, 2008.
U.S. Appl. No. 12/147,093, filed Jun. 26, 2008.
U.S. Appl. No. 12/181,504, filed Jul. 29, 2008.
U.S. Appl. No. 12/184,556, filed Aug. 1, 2008.
U.S. Appl. No. 12/194,254, filed Aug. 19, 2008.
U.S. Appl. No. 12/197,601, filed Aug. 25, 2008.
U.S. Appl. No. 12/197,405, filed Aug. 25, 2008.
U.S. Appl. No. 12/197,473, filed Aug. 25, 2008.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.
U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/251,857, filed Oct. 15, 2008.
U.S. Appl. No. 12/253,457, filed Oct. 17, 2008.
U.S. Appl. No. 12/366,298, filed Feb. 5, 2009.
U.S. Appl. No. 12/389,906, filed Feb. 20, 2009.
U.S. Appl. No. 12/389,915, filed Feb. 20, 2009.
U.S. Appl. No. 12/401,268, filed Mar. 10, 2009.
U.S. Appl. No. 12/416,583, filed Apr. 1, 2009.
U.S. Appl. No. 12/419,395, filed Apr. 7, 2009.
U.S. Appl. No. 12/423,609, filed Apr. 14, 2009.
U.S. Appl. No. 12/434,903, filed May 4, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
U.S. Appl. No. 12/487,917, filed Jun. 19, 2009.
U.S. Appl. No. 12/493,302, filed Jun. 29, 2009.
U.S. Appl. No. 12/504,738, filed Jul. 17, 2009.
U.S. Appl. No. 12/508,700, filed Jul. 24, 2009.
U.S. Appl. No. 12/535,851, filed Aug. 5, 2009.
U.S. Appl. No. 12/535,856, filed Aug. 5, 2009.
U.S. Appl. No. 12/536,616, filed Aug. 6, 2009.
U.S. Appl. No. 12/542,348, filed Aug. 17, 2009.
U.S. Appl. No. 12/542,785, filed Aug. 18, 2009.
U.S. Appl. No. 12/547,155, filed Aug. 25, 2009.
U.S. Appl. No. 12/548,644, filed Aug. 27, 2009.
U.S. Appl. No. 12/555,576, filed Sep. 8, 2009.
U.S. Appl. No. 12/556,010, filed Sep. 9, 2009.
U.S. Appl. No. 12/561,096, filed Sep. 16, 2009.
U.S. Appl. No. 12/562,575, filed Sep. 18, 2009.
U.S. Appl. No. 12/562,842, filed Sep. 18, 2009.
U.S. Appl. No. 12/566,299, filed Sep. 24, 2009.
U.S. Appl. No. 12/568,067, filed Sep. 28, 2009.
U.S. Appl. No. 12/568,524, filed Sep. 28, 2009.
U.S. Appl. No. 12/568,551, filed Sep. 28, 2009.
U.S. Appl. No. 12/568,777, filed Sep. 29, 2009.
U.S. Appl. No. 12/568,838, filed Sep. 29, 2009.
U.S. Appl. No. 12/568,883, filed Sep. 29, 2009.
U.S. Appl. No. 12/568,972, filed Sep. 29, 2009.
U.S. Appl. No. 12/569,171, filed Sep. 29, 2009.
U.S. Appl. No. 12/569,685, filed Sep. 29, 2009.
U.S. Appl. No. 12/582,857, filed Oct. 21, 2009.
U.S. Appl. No. 12/606,769, filed Oct. 27, 2009.
U.S. Appl. No. 12/607,221, filed Oct. 28, 2009.
U.S. Appl. No. 12/607,268, filed Oct. 28, 2009.

(56) References Cited

OTHER PUBLICATIONS

U.S. Appl. No. 12/619,462, filed Nov. 16, 2009.
U.S. Appl. No. 12/620,289, filed Nov. 17, 2009.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic ® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With The LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94 ln Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunitie—Part I", (2001) J Vasc. Interv. Radiol, vol. 12, pp. 1021-1032.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Humphries Jr. et al., "Finite Element Codes to Model Electrical Heating and Non Linear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure™ Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure™ Vessel Sealing System in Hemorrhoidectormy" American College of Surgeons (ACS) Clinic La Congress Poster (2000).
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, pp. 205-210.
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.

(56) References Cited

OTHER PUBLICATIONS

Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I Peg) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.

Solbiati et al., (2001) "Percutaneous Radio-frequency Ablation of Hepatic Metastases from Colorectal Cancer: Long-term Results in 117 Patients", Radiology, vol. 221, pp. 159-166.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817-825.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.

(56) References Cited

OTHER PUBLICATIONS

European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08011282 dated Aug. 14, 2009.
European Search Report EP 08011705 dated Aug. 20, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08169973.8 dated Apr. 6, 2009.
European Search Report EP 09156861.8 dated Aug. 4, 2009.
European Search Report EP 09161502.1 dated Sep. 2, 2009.
European Search Report EP 09166708 dated Oct. 15, 2009.
International Search Report PCT/US98/18640 dated Jan. 29, 1998.
International Search Report PCT/US98/23950 dated Jan. 14, 1998.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US05/36168 dated Aug. 28, 2006.
International Search Report PCT/US08/052460 dated Apr. 24, 2008.
International Search Report PCT/US09/31658 dated Mar. 11, 2009.
Esterline Product Literature, "Light Key: Visualize a Virtual Keyboard. One With No Moving Parts", Nov. 1, 2003; 4 pages.
Urologix, Inc.—Medical Professionals: Targis™ Technology. "Overcoming the Challenge" located at: <http://www.urologix.com/medical.technology.html > Nov. 18, 1999; 3 pages.
Japanese Office Action mailed Mar. 11, 2014 from Application No. JP 2010-206705.

* cited by examiner

TISSUE ABLATION SYSTEM WITH ENERGY DISTRIBUTION

BACKGROUND

1. Technical Field

The present disclosure relates to apparatus and methods for providing energy to tissue and, more particularly, to devices and electromagnetic radiation delivery procedures utilizing ablation probes and methods of controlling the delivery of electromagnetic radiation to tissue.

2. Discussion of Related Art

Treatment of certain diseases requires destruction of malignant tumors. Electromagnetic radiation can be used to heat and destroy tumor cells. Treatment may involve inserting ablation probes into tissues where cancerous tumors have been identified. Once the probes are positioned, electromagnetic energy is passed through the probes into surrounding tissue.

In the treatment of diseases such as cancer, certain types of cancer cells have been found to denature at elevated temperatures that are slightly lower than temperatures normally injurious to healthy cells. Known treatment methods, such as hyperthermia therapy, use electromagnetic radiation to heat diseased cells to temperatures above 41° C. while maintaining adjacent healthy cells below the temperature at which irreversible cell destruction occurs. These methods involve applying electromagnetic radiation to heat, ablate and/or coagulate tissue. Microwave energy is sometimes utilized to perform these methods. Other procedures utilizing electromagnetic radiation to heat tissue also include coagulation, cutting and/or ablation of tissue.

Electrosurgical devices utilizing electromagnetic radiation have been developed for a variety of uses and applications. A number of devices are available that can be used to provide high bursts of energy for short periods of time to achieve cutting and coagulative effects on various tissues. There are a number of different types of apparatus that can be used to perform ablation procedures. Typically, microwave apparatus for use in ablation procedures include a microwave generator, which functions as an energy source, and a microwave surgical instrument having an antenna assembly for directing the energy to the target tissue. The microwave generator and surgical instrument are typically operatively coupled by a cable assembly having a plurality of conductors for transmitting microwave energy from the generator to the instrument, and for communicating control, feedback and identification signals between the instrument and the generator.

Microwave energy is typically applied via antenna assemblies that can penetrate tissue. Several types of antenna assemblies are known, such as monopole and dipole antenna assemblies. In monopole and dipole antenna assemblies, microwave energy generally radiates perpendicularly away from the axis of the conductor. A monopole antenna assembly includes a single, elongated conductor that transmits microwave energy. A typical dipole antenna assembly has two elongated conductors, which are linearly aligned and positioned end-to-end relative to one another with an electrical insulator placed therebetween. Each conductor may be about ¼ of the length of a wavelength of the microwave energy, making the aggregate length of the two conductors about ½ of the wavelength of the supplied microwave energy. During certain procedures, it can be difficult to assess the extent to which the microwave energy will radiate into the surrounding tissue, making it difficult to determine the area or volume of surrounding tissue that will be ablated.

SUMMARY

According to an embodiment of the present disclosure, a microwave ablation system includes an energy source adapted to generate microwave energy and a power splitting device having an input adapted to connect to the energy source and a plurality of outputs. The plurality of outputs are configured to be coupled to a corresponding plurality of energy delivery devices. The power splitting device is configured to selectively divide energy provided from the energy source between the plurality of energy devices.

According to another embodiment of the present disclosure, a microwave ablation system includes an energy source adapted to generate microwave energy and a power splitting device having an input adapted to connect to the energy source and a plurality of outputs. The plurality of outputs are configured to be coupled to a corresponding plurality of energy delivery devices via corresponding transmission lines. The power splitting device is configured to selectively divide energy provided from the energy source between the plurality of energy delivery devices either equally or unequally.

According to another embodiment of the present disclosure, a method for providing energy to a target tissue includes the steps of positioning a plurality of energy delivery devices into a portion of the target tissue and selectively dividing energy on a plurality of channels to at least one of the energy delivery devices. The method also includes applying energy from one or more of the energy delivery devices to the target tissue.

DETAILED DESCRIPTION

Figure 1:
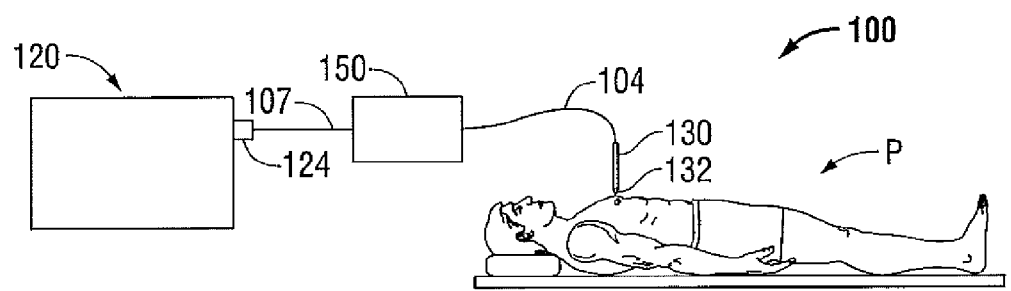
FIG. 1 is a schematic diagram of an electrosurgical system for treating tissue, according to an embodiment of the present disclosure.

Hereinafter, embodiments of the presently disclosed tissue ablation systems are described with reference to the accompanying drawings. Like reference numerals may refer to similar or identical elements throughout the description of the figures. As used herein, the term "microwave" generally refers to electromagnetic waves in the frequency range of 300 megahertz (MHz) (3×10⁸ cycles/second) to 300 gigahertz (GHz) (3×10" cycles/second). As used herein, the phrase "transmission line" generally refers to any transmission medium that can be used for the propagation of signals from one point to another (including, but not limited to coaxial cables, waveguides etc.).

Various embodiments of the present disclosure provide electrosurgical systems for treating tissue and methods of controlling the delivery of electromagnetic radiation to tissue.

Embodiments may be implemented using electromagnetic radiation at microwave frequencies or at other frequencies. Electrosurgical systems for treating tissue, according to various embodiments of the present disclosure, deliver microwave power to a plurality of electrosurgical devices. Electrosurgical devices, such as ablation probes, for implementing embodiments of the present disclosure may be inserted directly into tissue, inserted through a lumen, such as a vein, needle or catheter, placed into the body during surgery by a clinician, or positioned in or on the body by other suitable methods known in the art.

FIG. 1 is a schematic diagram of an electrosurgical system for treating tissue, according to one embodiment of the present disclosure. Referring to FIG. 1, the electrosurgical system 100 includes an electrosurgical generator 120 for generating an output signal, a power splitter 150 coupled to the electrosurgical generator 120, and an electrosurgical instrument or device 130 coupled to the power splitter 150. The power splitter 150 is coupled to a transmission line 107 that electrically connects the power splitter 150 to an output 124 on the electrosurgical generator 120. The device 130 includes an antenna assembly 132 for delivery of electromagnetic radiation, coupled to a transmission line 104 that electrically connects the antenna assembly 132 to the power splitter 150. Although not shown as such in FIG. 1, device 130 may include a plurality of antenna assemblies.

The electrosurgical generator 120 may include other input or output devices such as knobs, dials, switches, buttons, graphical user interfaces, displays, and the like for control, indication and/or operation. The electrosurgical generator 120 may be capable of generating a plurality of output signals of various frequencies that are input to the power splitter 150. In one embodiment, the electrosurgical generator 120 generates a plurality of microwave signals at substantially the same frequency. The electrosurgical generator 120 may include a control unit (not shown) that controls operations of the electrosurgical generator 120, such as time of operation, power output and/or the mode of electrosurgical operation, which may have been selected by the clinician.

The electrosurgical system 100 may include a footswitch (not shown) coupled to the electrosurgical generator 120. When actuated, the footswitch causes the electrosurgical generator 120 to generate microwave energy. The device 130 may include knobs, dials, switches, buttons or the like (not shown) to communicate to the electrosurgical generator 120 to adjust or select from a number of configuration options for delivering energy. Utilizing knobs, dials, switches or buttons on the device 130 and/or a footswitch enables the clinician to activate the electrosurgical generator 120 to energize the device 130 while remaining near the patient P regardless of the location of the electrosurgical generator 120.

Although not shown as such in FIG. 1, electrosurgical system 100 may include a plurality of channels defined by a plurality of electrosurgical devices and a plurality of transmission lines that electrically connect the electrosurgical devices to the power splitter 150. In an embodiment, the power splitter 150 is capable of monitoring the phase of each channel and adjusting the phase of the signal in each channel with respect to the other channel(s) to a predetermined phase relationship. The power splitter 150 provides a plurality of signals to the device 130 in a set of phase relationships between the signals. Although the power splitter 150 is illustrated as a standalone module in FIG. 1, it is to be understood that the power splitter 150 may be integrated fully or partially into the electrosurgical generator 120, the device 130, and/or other devices. Furthermore, it may be appreciated that electrosurgical generator 120, output 124, transmission lines 107 and 104 and power splitter 150 could be integrated within device 130, thus obviating the need for separate elements.

The antenna assembly 132 includes multiple antennas and/or multiple antenna elements, each driven by an output signal of the power splitter 150. The antenna assembly 132 may also include multiple antenna circuits, each driven by an output signal of the power splitter 150.

In embodiments, the antenna assembly 132 is a microwave antenna configured to allow direct insertion or penetration into tissue of the patient P. The antenna assembly 132 may be axially rigid to allow for tissue penetration. The antenna assembly 132 is sufficiently small in diameter to be minimally invasive of the body, which may reduce the preparation of the patient P as might be required for more invasive penetration of the body. The antenna assembly 132 is inserted directly into tissue, inserted through a lumen, such as, for example, a vein, needle or catheter, placed into the body during surgery by a clinician, or positioned in the body by other suitable methods.

Figure 2:
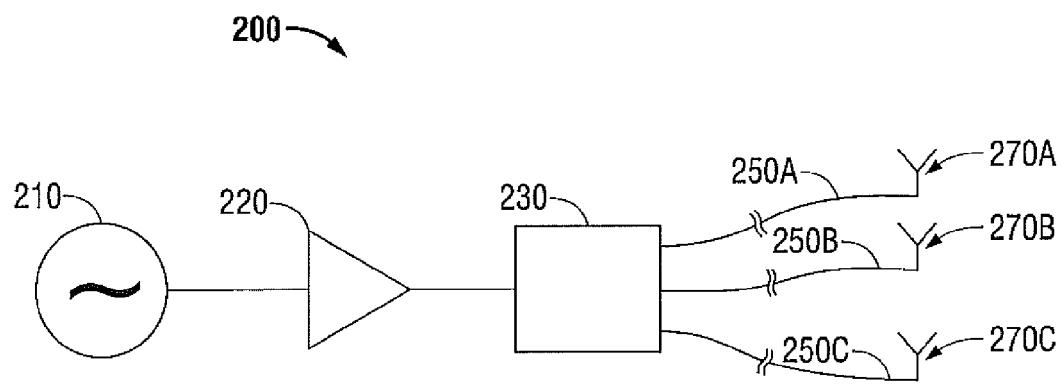
FIG. 2 is a schematic diagram of an electrosurgical system for treating tissue, according to one embodiment of the present disclosure.

FIG. 2 is a schematic diagram of an electrosurgical system for treating tissue, according to another embodiment of the present disclosure. Referring to FIG. 2, the electrosurgical system 200 includes a microwave signal source 210 providing a microwave frequency output signal to a microwave amplifier unit 220, a microwave power splitter 230 coupled to the microwave amplifier unit 220, and a first, a second and a third microwave ablation antenna assembly 270A, 270B and 270C, each coupled to the microwave power splitter 230. The microwave signal source 210 is capable of generating a plurality of output signals of various frequencies that are input to the microwave amplifier unit 220. The microwave amplifier unit 220 may have any suitable input power and output power.

In the electrosurgical system 200, a first transmission line 250A electrically connects the first antenna assembly 270A to the microwave power splitter 230, defining a first channel; a second transmission line 250B electrically connects the second antenna assembly 270B to the microwave power splitter 230, defining a second channel; and a third transmission line 250C electrically connects the third antenna assembly 270C to the microwave power splitter 230, defining a third channel. The first, second and third transmission lines 250A, 250B and 250C may each include one or more electrically conductive elements, such as electrically conductive wires.

In an embodiment, the first, second, and third transmission lines 250A, 250B and 250C each have substantially the same length, which preserves the phase relationship between the electrical signals in each channel of the electrosurgical system 200. It is to be understood that "length" may refer to electrical length or physical length. In general, electrical length is an expression of the length of a transmission medium in terms of the wavelength of a signal propagating within the medium. Electrical length is normally expressed in terms of wavelength, radius, or degrees. For example, electrical length may be expressed as a multiple or sub-multiple of the wavelength of an electromagnetic wave or electrical signal propagating within a transmission medium. The wavelength may be expressed in radians or in artificial units of angular measure, such as degrees. The microwave power splitter 230 may be implemented by any suitable power divider that provides equal or unequal power split at the output ports of the microwave power splitter 230 while substantially maintaining phase and amplitude balance. For example, the microwave power splitter 230 may be implemented using a 3-way power divider that provides equal or unequal power split at its output ports while maintaining a phase balance of <+/−45 degrees.

Each antenna assembly 270A, 270B and 270C typically includes a rigid or bendable needle or needle-like structure.

The antenna assemblies 270A, 270B and 270C are positioned substantially parallel to each other, for example, spaced about 5 millimeters (mm) apart, and inserted directly into tissue or placed into the body during surgery by a clinician, or positioned in the body by other suitable methods. Although the electrosurgical system 200 illustrated in FIG. 2 includes three microwave ablation antenna assemblies 270A, 270B and 270C, it is to be understood that any "N" number of antenna assemblies may be utilized and that microwave power splitter 230 may be implemented by any suitable power divider that divides or splits a microwave input signal into "N" number of output signals of equal or unequal power.

The electrosurgical system 200 delivers microwave power to one or more antenna assemblies 270A, 270B and 270C of the three-channel system. The electrosurgical system 200 may deliver substantially in-phase microwave power to each antenna assembly 270A, 270B and 270C. By controlling the phase of ablation probes with respect to each other, according to embodiments of the present disclosure, a desired effect on tissue between the probes is produced. In ablation procedures using in-phase probes, according to various embodiments of the present disclosure, there may be a reduction in energy that might otherwise move between the antenna shafts toward the surface with out-of-phase probes.

In an embodiment, the electrosurgical system 200 is implemented with operating frequencies in the range of about 300 MHz to about 5 GHz, which may be useful in performing ablation procedures and/or other procedures. It is to be understood that the electrosurgical system 200 may be implemented with any appropriate range of operating frequencies.

In another embodiment, the electrosurgical system 200 delivers microwave power to particular channels individually or any combination of one or more channels equally or unequally. The microwave signal source 210 and/or antenna assembly 270A, 270B and 270C may include input or output devices such as knobs, dials, switches, buttons, graphical user interfaces, displays, and the like to facilitate selective activation of energy delivery to particular channels or combination of channels. For example, a user may select channels to which energy is delivered. In this scenario, if the second and third channels are selected, energy delivery may be divided equally (e.g., P/2) between the second and third channels and, thus, unequally between the first channel and the second and third channels since no energy is delivered to the first channel in this scenario. Further, in this scenario, energy may be delivered to individual channels according to selected time intervals by dynamically changing the channels to which energy is delivered. For example, energy may be delivered to the first channel at a time interval t1. At a subsequent time interval t2, energy is delivered to the first channel and the third channel. At a subsequent time interval t3, energy delivery to the first channel is stopped and energy delivery to the third channel continues. At a subsequent time interval t4, energy delivery to all channels is stopped.

In another embodiment, the microwave power splitter 230 divides energy between the antenna assemblies 270A, 270B and 270C to tailor the size and shape of ablation lesions. With this purpose in mind, electrosurgical system 200 may include a suitable storage device (not shown) integrated within the microwave signal source 210, the microwave power splitter 230, or be a stand-alone device, that is configured to store settings or data corresponding to particular ablation geometries (e.g., ablation images, antenna tip geometries, power division settings, power amplitude settings, etc.). Based on the stored settings or data, the microwave signal source 210 modifies delivery of microwave power to the microwave power splitter 230 and/or the microwave power splitter 230 modifies the division of microwave power between the channels to achieve the desired ablation geometry.

Figure 3:
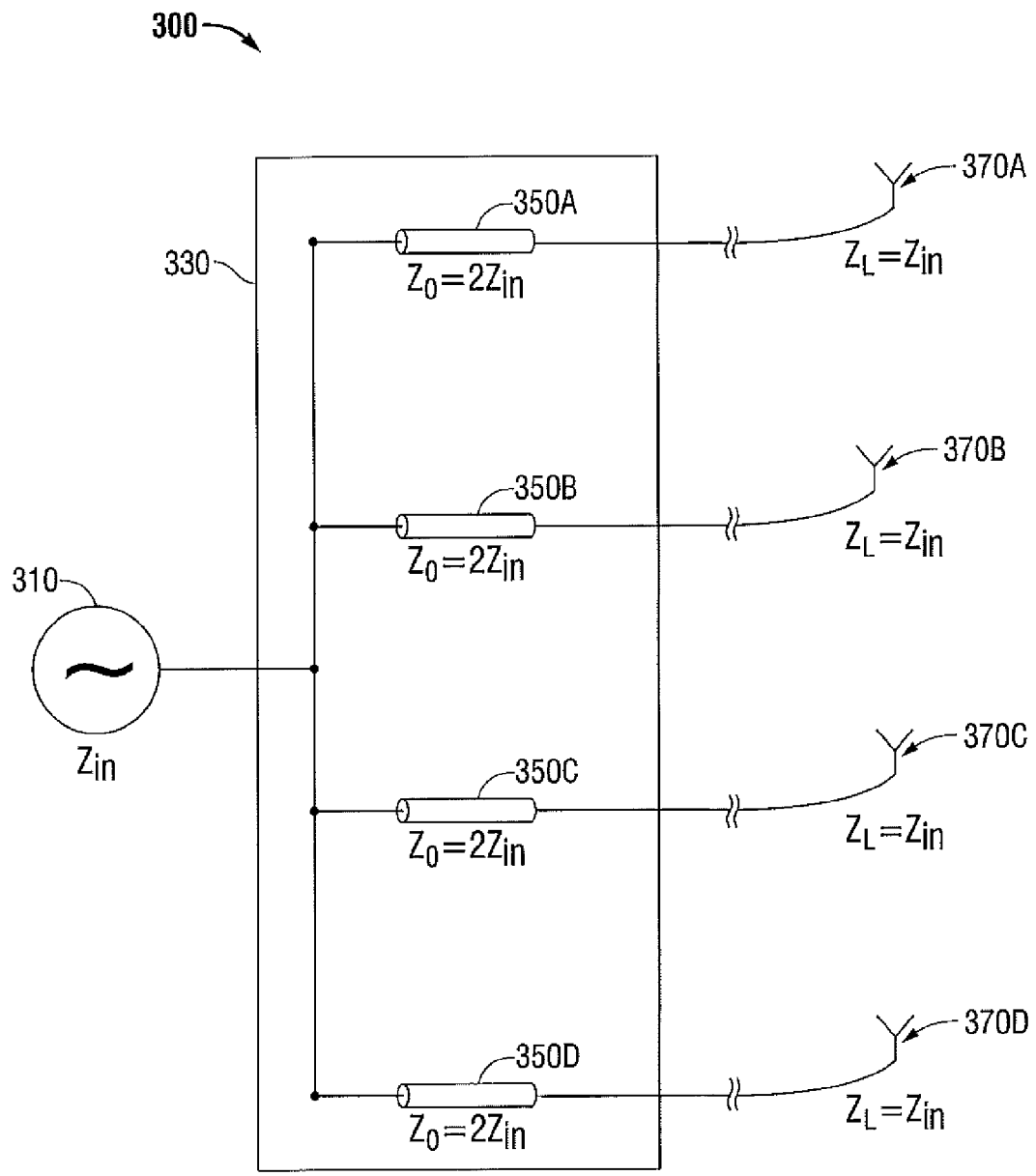
FIG. 3 is a schematic diagram of an electrosurgical system for treating tissue, according to another embodiment of the present disclosure.

FIG. 3 is a schematic diagram of an electrosurgical system for treating tissue, according to an embodiment of the present disclosure. Referring to FIG. 3, the electrosurgical system 300 includes a microwave signal source 310 providing a microwave frequency output signal to a microwave power splitter 330, and a first, a second, a third, and a fourth microwave ablation antenna assembly 370A, 370B, 370C, and 370C, each coupled to the microwave power splitter 330. The microwave signal source 310 is capable of generating a plurality of output signals of various frequencies that are input to the microwave power splitter 330.

The microwave power splitter 330 includes a first quarter wavelength transmission line 350A that electrically connects the first antenna assembly 370A to the microwave signal source 310, defining a first channel; a second quarter wavelength transmission line 350B that electrically connects the second antenna assembly 370B to the microwave signal source 310, defining a second channel; a third quarter wavelength transmission line 350C that electrically connects the third antenna assembly 370C to the microwave signal source 310, defining a third channel; and a fourth transmission line 350D that electrically connects the fourth antenna assembly 370D to the microwave signal source 310, defining a fourth channel. Transmission lines 350A, 350B, 350C, and 350D each include one or more electrically conductive elements, such as electrically conductive wires. In an embodiment, transmission lines 350A, 350B, 350C, and 350D each have substantially the same length, which preserves the phase relationship between electrical signals in each channel of the electrosurgical system 300.

As is known in the art, for maximum power transfer between a power source (e.g., microwave signal source 310) and a load (e.g., antenna assemblies 370A, 370B, 370C, 370D), the load impedance must be equal to the source impedance. For the case wherein the transmission line between the power source and the load is quarter wavelength, as described with reference to the embodiment of FIG. 3, an impedance of the microwave signal source 310 is calculated using the following equation (1):

$$Z_{in} = Z_o^2 / Z_L \tag{1}$$

In equation (1), $Z_{in}$ is the input impedance to the quarter wavelength transmission lines 350A, 350B, 350C, and 350D (e.g., the impedance at the microwave signal generator 310), $Z_o$ is the characteristic impedance of the quarter wavelength transmission lines 350A, 350B, 350C, and 350D (e.g., the impedance at the microwave power splitter 330), and $Z_L$ is the impedance of the antenna assemblies 370A, 370B, 370C, 370D. Applying equation (1) to the illustrated embodiment of FIG. 3, yields the following equation (2) to account for the four inputs to the quarter wavelength transmission lines 350A, 350B, 350C, and 350D:

$$4 * Z_{in} = Z_o^2 / Z_L \tag{2}$$

Since $Z_L$ must equal $Z_{in}$ to achieve maximum power transfer, as discussed hereinabove, solving for the characteristic impedance $Z_o$ of the quarter wavelength transmission line yields the following equation (3):

$$Z_o = 2 * Z_{in} \tag{3}$$

By way of example, given that $Z_L = Z_{in} = 50$ ohms, the characteristic impedance $Z_o$ of the transmission lines 350A, 350B, 350C, and 350D is equal to 100 ohms, and the electrical length of the transmission lines 350A, 350B, 350C, and 350D is set to a quarter wavelength, the load impedance $Z_L$ of the antenna assemblies 370A, 370B, 370C, 370D at the input of the power splitter 330 is transformed from 50 ohms, which corresponds to a full wavelength, to 200 ohms, which corresponds to a quarter wavelength (i.e., 50 ohms/0.25=200 ohms). Since the four antenna assemblies 370A, 370B, 370C, 370D are in parallel with microwave signal generator 310, the equivalent resistance $Z_L$ of the antenna assemblies 370A, 370B, 370C, 370D is equal to 200 ohms divided by four antenna assemblies or 50 ohms. Since $Z_{IN}$=50 ohms=$Z_L$, maximum power transfer will occur between microwave signal generator 310 and each of antenna assemblies 370A, 370B, 370C, 370D.

Although the electrosurgical system 300 illustrated in FIG. 3 includes four microwave ablation antenna assemblies 370A, 370B, 370C, and 370D and four quarter wavelength transmission lines 350A, 350B, 350C, and 350D, it is to be understood that any N number of antenna assemblies and any N number of quarter wavelength transmission lines may be utilized.

Figure 4:
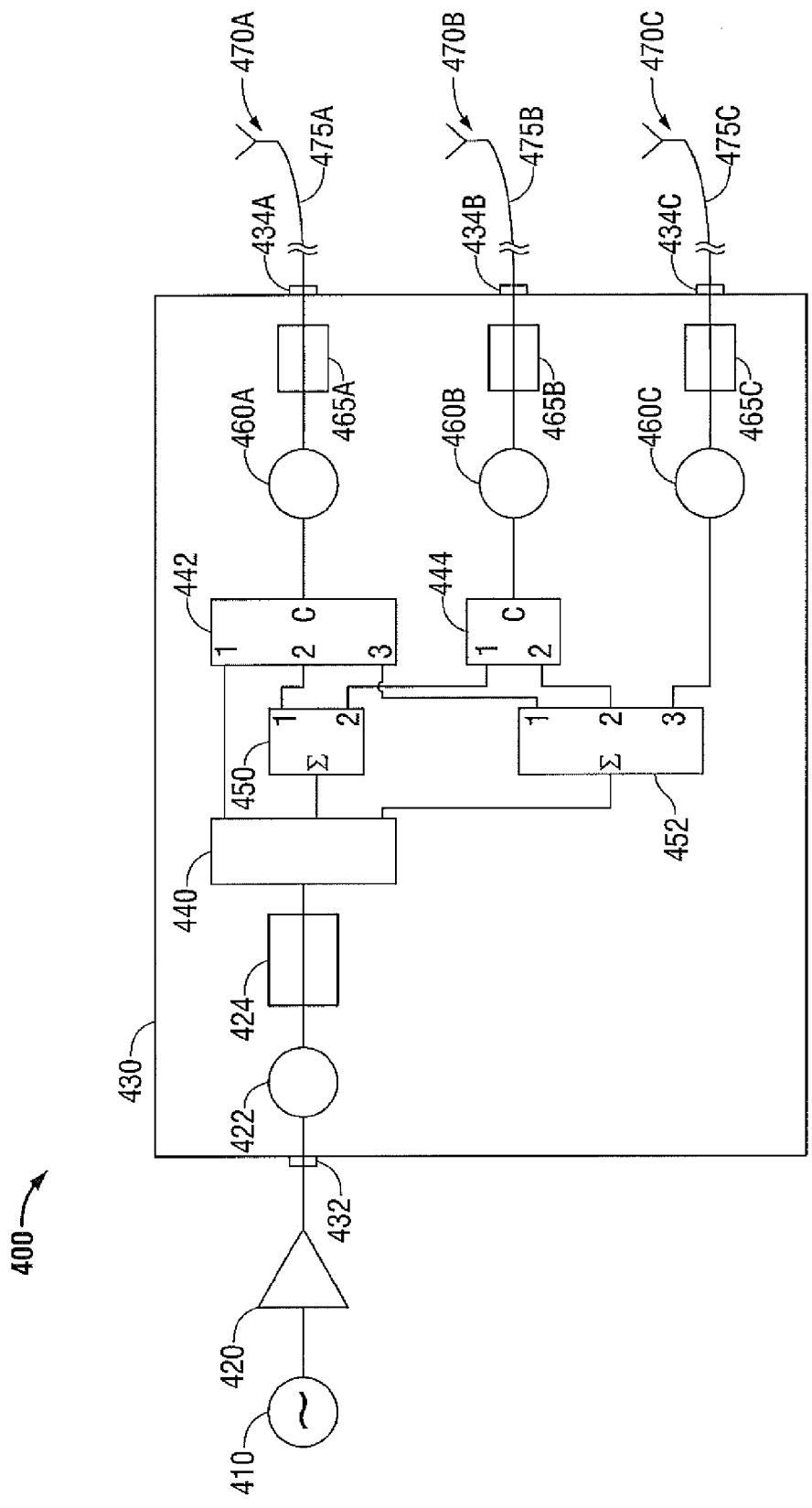
FIG. 4 is a schematic diagram of an electrosurgical system for treating tissue, according to another embodiment of the present disclosure.

FIG. 4 is a schematic diagram of an electrosurgical system 400 for treating tissue, according to another embodiment of the present disclosure. Referring to FIG. 4, the electrosurgical system 400 illustrated is a three-channel system that includes a microwave signal source 410, a microwave amplifier 420, a first, a second, and a third microwave ablation antenna assembly 470A, 470B, and 470C, and a controller 430 that includes one input 432 and a first, a second, and a third output 434A, 434B, and 448C.

The electrosurgical system 400 includes a first transmission line 475A that electrically connects the first antenna assembly 470A to the first output 434A, defining a first channel; a second transmission line 475B that electrically connects the second antenna assembly 470A to the second output 434B, defining a second channel; and a third transmission line 475C that electrically connects the third antenna assembly 470C to the third output 434C, defining a third channel. The first, second, and third transmission lines 475A, 475B, and 475C each include one or more electrically conductive elements, such as electrically conductive wires. In an embodiment, the first, second, and third transmission lines 475A, 475B, and 475C each have substantially the same length, which preserves the phase relationship between electrical signals in each channel of the electrosurgical system 400.

The microwave signal source 410 provides a microwave frequency output signal to the amplifier 420. The microwave amplifier 420 provides an output signal through an output terminal that is electrically coupled to the input 432 of the controller 430. Although the amplifier 420 is illustrated as a standalone module in FIG. 4, it is to be understood that the amplifier 420 may be integrated fully or partially into the controller 430. Controller 430 includes a first output-side directional coupler 465A, a second output-side directional coupler 465B, and a third output-side directional coupler 465C. Output-side directional couplers 465A, 465B, 465C are configured to measure power at each output 434A, 434B, 434C, respectively, and to transmit a microwave signal, received as input, to antenna assemblies 470A, 470B, and 470C.

The controller 430 includes a first isolator 422 electrically coupled between the input 432 and an input-side directional coupler 424. The first isolator 422 operates to appear as a fixed matching load to the microwave signal source 410 to prevent detuning thereof due to variations in load impedance caused by, for example, antenna assemblies 470A, 470B, and 470C and/or transmission lines 475A, 475B, and 475C. The first isolator 422 transmits the microwave signal from the amplifier 420 to the input-side directional coupler 424. The input-side directional coupler 424 measures the microwave signal received from the amplifier 420 as input and transmits the microwave signal to a first switching device 440 electrically coupled thereto. The first switching device 440 transmits the microwave signal to any one or more of a 1:2 power divider 450, a 1:3 power divider 452, and/or a second switching device 442, individually or in any combination thereof.

Upon receiving the microwave signal from switching device 440, power divider 450 divides the microwave signal as output between the second switching device 442 and a third switching device 444. Upon receiving the microwave signal from switching device 440, power divider 452 divides the microwave signal as output between the second switching device 442, the third switching device 444, and the third output-side directional coupler 465C. The third output-side directional coupler 465C powers antenna assembly 470C by transmitting the microwave signal received from power divider 452 to the third output 434C.

Upon receiving the microwave signal from any combination of the first switching device 440, power divider 450, and/or power divider 452, the second switching device 442 transmits the microwave signal to the first output-side directional coupler 465A. The first output-side directional coupler 465A powers antenna assembly 470A by transmitting the microwave signal received from the second switching device 442 to the first output 434A.

Upon receiving the microwave signal from any combination of power divider 450 and/or 452, the third switching device 444 transmits the microwave signal to the second output-side directional coupler 465B. The second output-side directional coupler 465B powers antenna assembly 470B by transmitting the microwave signal received from the third switching device 444 to the second output 434B.

In operation of electrosurgical system 400, depending on the configuration of switching devices 440, 442, and 444, the output power values corresponding to the three outputs 434A, 434B, and 434C for a given power P will be either P, 0, and 0; P/2, P/2, and 0; or P/3, P/3, and P/3.

Controller 430 further includes a first isolator 460A electrically coupled between the second switching device 442 and the first output-side directional coupler 465A; a second isolator 460B electrically coupled between the third switching device 444 and the second output-side directional coupler 465B; and a third isolator 460C electrically coupled between power divider 452 and the third output-side directional coupler 465C. First, second, and third isolators 460A, 460B, and 460C are configured to appear as a fixed matching load to the microwave signal generator 410 to prevent detuning thereof due to variations in load impedance caused by, for example, antenna assemblies 470A, 470B, and 470C and/or transmission lines 475A, 475B, and 475C.

Switching devices 440, 442, 444 may be any suitable switching device configured to output power to a load connected thereto based on more than one inputs such as, for example, a single pole double throw switch (SPDT), a single pole triple throw switch (SP3T), etc.

In embodiments, any one or more of isolator 422 and isolators 460A, 460B, 460C may be a three-port circulator, as is known in the art, having one of its three ports terminated in a fixed matching load to the microwave signal source 410 to effectively operate substantially as described above with reference to isolator 422 and/or isolators 460A, 460B, 460C.

The controller 430 may include one or more phase detectors (not shown) to compare the respective phases of electrical signals inputted through the input 432. By comparing a reference signal, such as a clock signal, to a feedback signal using a phase detector, phase adjustments may be made based on the comparison of the electrical signals inputted, to set the phase relationship between electrical signals in each channel of the electrosurgical system 400.

In an embodiment, the controller 440 delivers phase-controlled microwave power through the outputs 434A, 434B and 434C to the antenna assemblies 470A, 470B and 470C, respectively, irrespective of the phase of the electrical signal inputted through the input 432.

Figure 5:
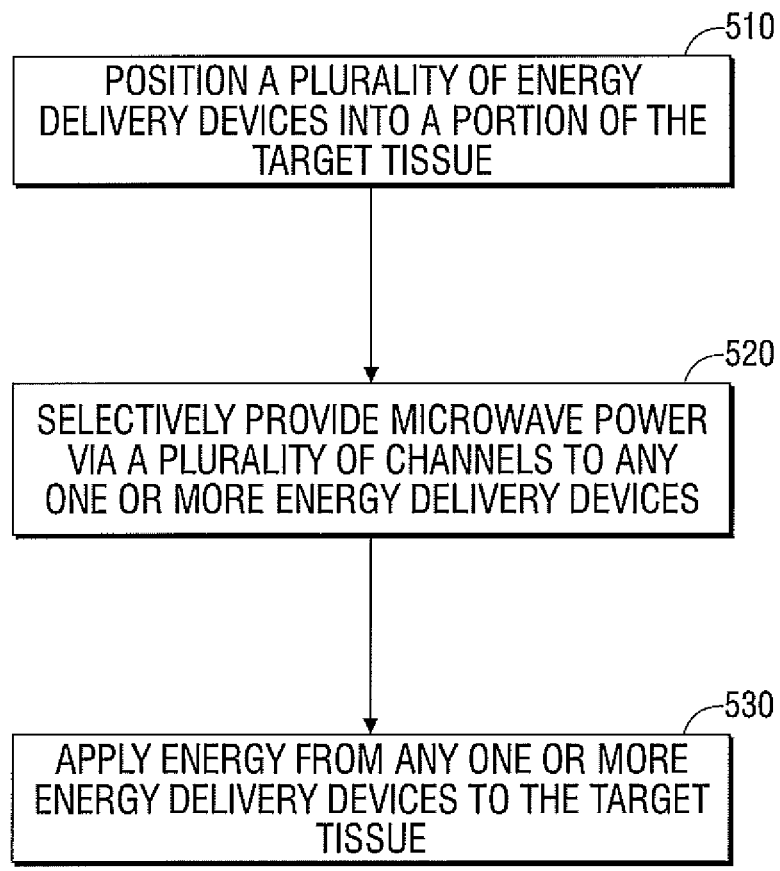
FIG. 5 is a block diagram illustrating a method for treating tissue, according to an embodiment of the present disclosure.

FIG. 5 is a flowchart illustrating a method for providing energy to a target tissue, according to an embodiment of the present disclosure. Referring to FIG. 5, in step 510, a plurality of energy delivery devices are positioned into a portion of the target tissue. The energy delivery devices may be implemented using any suitable electrosurgical instruments or devices, such as, for example, the device 130, according to embodiments of the present disclosure described in connection with FIG. 1.

The energy delivery devices are positioned into a portion of a target site on the tissue or adjacent to a portion of a target site on the tissue. The energy delivery devices are inserted directly into tissue, inserted through a lumen, such as a vein, needle or catheter, placed into the body during surgery by a clinician or positioned in the body by other suitable methods. The energy delivery devices include any suitable antenna assemblies for the delivery of electromagnetic radiation, such as, for example, the antenna assemblies 270A, 270B and 270C, according to embodiments of the present disclosure described in connection with FIG. 2.

In step 520, microwave power is selectively transmitted on a plurality of channels to any one or more of the energy delivery devices. The microwave power may be transmitted to the energy delivery devices from the microwave power splitter 230, according to embodiments of the present disclosure described in connection with FIG. 2, the microwave power splitter 330, according to embodiments of the present disclosure described in connection with FIG. 3, or the controller 440, according to embodiments of the present disclosure described in connection with FIG. 4.

In step 530, microwave energy from any one or more energy delivery devices is applied to the target tissue.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A microwave ablation system, comprising: an energy source adapted to generate microwave energy; a first power splitting device and a second power splitting device, each of the first and second power splitting devices having an input adapted to connect to the energy source and a plurality of outputs; and a plurality of energy delivery devices each including an elongated needle structure configured to be inserted directly into tissue, the plurality of energy delivery devices adapted to electrically communicate with the plurality of outputs of at least one of the first or second power splitting devices; wherein the first and second power splitting devices are configured to selectively divide energy provided from the energy source between the plurality of energy delivery devices, the first power splitting device configured to selectively divide energy from the energy source between at least two of the plurality of energy delivery devices, and the second power splitting device configured to selectively divide energy from the energy source between the at least two energy delivery devices and another energy delivery device from the plurality.

2. A microwave ablation system according to claim 1, wherein energy is selectively divided equally between the plurality of energy delivery devices.

3. A microwave ablation system according to claim 1, wherein energy is selectively divided unequally between the plurality of energy delivery devices.

4. A microwave ablation system according to claim 1, wherein energy is selectively divided between the plurality of energy delivery devices based on at least one pre-determined time interval.

5. A microwave ablation system according to claim 1, wherein energy is selectively divided between the plurality of energy delivery devices based on a desired ablation geometry.

6. A microwave ablation system according to claim 1, wherein energy from the energy source is provided to the plurality of energy delivery devices via a corresponding plurality of transmission lines.

7. A microwave ablation system according to claim 6, wherein the plurality of transmission lines are substantially equal in length to each other.

8. A microwave ablation system according to claim 6, wherein each of the plurality of transmission lines has a length of a quarter wavelength.

9. A microwave ablation system according to claim 1, further comprising at least one switching device configured to selectively deliver energy from the energy source to at least one of the first or second power splitting devices.

10. A microwave ablation system according to claim 9, wherein the at least one switching device is one of a single pole double throw switch or a single pole triple throw switch.

11. A microwave ablation system according to claim 1, further comprising at least one isolator configured to provide a fixed load relative to the energy source.

12. A microwave ablation system according to claim 1, further comprising at least one directional coupler configured to measure power at the input of each of the first and second power splitting devices and at least one other directional coupler configured to measure power at the plurality of outputs of each of the first and second power splitting devices.

13. A microwave ablation system, comprising: an energy source adapted to generate microwave energy; a first power splitting device and a second power splitting device, each of the first and second power splitting devices having an input adapted to connect to the energy source and a plurality of outputs; and a plurality of energy delivery devices each including an elongated needle structure configured to be inserted directly into tissue, the plurality of energy delivery devices configured to electrically communicate with the plurality of outputs of at least one of the first or second power splitting devices via corresponding transmission lines; wherein the first and second power splitting devices are configured to selectively divide energy provided from the energy source either equally or unequally between the plurality of energy delivery devices, the first power splitting device configured to selectively divide energy from the energy source between at least two of the plurality of energy delivery devices, and the second power splitting device configured to selectively divide energy from the energy source between the at least two energy delivery devices and another energy delivery device from the plurality.

14. A microwave ablation system according to claim 13, wherein each energy delivery device of the plurality of energy delivery devices is a microwave ablation antenna.

* * * * *